US010537570B2

(12) United States Patent
Schummer et al.

(10) Patent No.: US 10,537,570 B2
(45) Date of Patent: Jan. 21, 2020

(54) USE OF PIMOBENDAN FOR THE REDUCTION OF HEART SIZE AND/OR THE DELAY OF ONSET OF CLINICAL SYMPTOMS IN PATIENTS WITH ASYMPTOMATIC HEART FAILURE DUE TO MITRAL VALVE DISEASE

(71) Applicant: Boehringer Ingelheim Vetmedica GmbH, Ingelheim am Rhein (DE)

(72) Inventors: Christoph Schummer, Weilrod (DE); Olaf Joens, Ober-Hilbersheim (DE)

( * ) Notice: Subject to any disclaimer, the term of this patent is extended or adjusted under 35 U.S.C. 154(b) by 0 days.

(21) Appl. No.: 15/477,188

(22) Filed: Apr. 3, 2017

(65) Prior Publication Data

US 2017/0290829 A1    Oct. 12, 2017

(30) Foreign Application Priority Data

Apr. 6, 2016  (EP) .................................... 16164041
Jun. 1, 2016  (EP) .................................... 16172394

(51) Int. Cl.
| | |
|---|---|
| *A61K 31/501* | (2006.01) |
| *A61K 31/55* | (2006.01) |
| *A61K 31/635* | (2006.01) |
| *A61K 31/50* | (2006.01) |
| *A61P 9/04* | (2006.01) |
| *A61K 9/20* | (2006.01) |

(52) U.S. Cl.
CPC ............ *A61K 31/501* (2013.01); *A61K 31/50* (2013.01); *A61K 31/55* (2013.01); *A61K 31/635* (2013.01); *A61P 9/04* (2018.01); *A61K 9/20* (2013.01); *A61K 2300/00* (2013.01)

(58) Field of Classification Search
CPC .... A61K 31/501; A61K 31/55; A61K 31/635; A61K 31/50
See application file for complete search history.

(56) References Cited

U.S. PATENT DOCUMENTS

| | | |
|---|---|---|
| 3,574,859 A | 4/1971 | Kosti |
| 3,822,349 A | 7/1974 | Kosti |
| 3,832,460 A | 8/1974 | Kosti |
| 3,839,522 A | 10/1974 | Kosti |
| 3,950,333 A | 4/1976 | Durant et al. |
| 4,128,658 A | 12/1978 | Price et al. |
| 4,256,743 A | 3/1981 | Goldhaber |
| 4,283,400 A | 8/1981 | von Bittera et al. |
| 4,283,408 A | 8/1981 | Hirata et al. |
| 4,293,557 A | 10/1981 | Shibata et al. |
| 4,361,563 A | 11/1982 | Austel et al. |
| 4,375,547 A | 3/1983 | Pioch |
| 4,386,099 A | 5/1983 | Cereda et al. |
| 4,427,648 A | 1/1984 | Brickl et al. |
| 4,569,837 A | 2/1986 | Suzuki et al. |
| 4,585,790 A | 4/1986 | Padfield et al. |
| 4,596,705 A | 6/1986 | Schepky et al. |
| 4,654,342 A | 3/1987 | Slater |
| 4,704,284 A | 11/1987 | Beatty et al. |
| 4,732,915 A | 3/1988 | Ayer et al. |
| 4,851,226 A | 7/1989 | Julian et al. |
| 4,865,851 A | 9/1989 | James et al. |
| 4,868,182 A | 9/1989 | Dage |
| 4,906,628 A | 3/1990 | Coates |
| 4,933,182 A | 6/1990 | Higashi et al. |
| 4,954,501 A | 9/1990 | Herter et al. |
| 4,973,469 A | 11/1990 | Mulligan et al. |
| 5,024,998 A | 6/1991 | Bodor |
| 5,151,420 A | 9/1992 | Backstrom et al. |
| 5,188,836 A | 2/1993 | Muhammad et al. |
| 5,364,646 A | 11/1994 | Gruber et al. |
| 5,569,657 A | 10/1996 | Nore et al. |
| 5,571,533 A | 11/1996 | Santus et al. |
| 6,407,079 B1 | 6/2002 | Muller et al. |
| 6,476,078 B1 | 11/2002 | Jerussi et al. |
| 6,669,955 B2 | 12/2003 | Chungi et al. |
| 6,713,487 B2 | 3/2004 | Yu et al. |
| 7,262,165 B2 | 8/2007 | Lindenblatt et al. |
| 8,409,612 B1 | 4/2013 | Criere et al. |
| 8,846,679 B2 | 9/2014 | Folger et al. |
| 8,980,894 B2 | 3/2015 | Daemmgen et al. |
| 2003/0059471 A1 | 3/2003 | Compton et al. |

(Continued)

FOREIGN PATENT DOCUMENTS

| | | |
|---|---|---|
| AU | 2012101682 A4 | 1/2013 |
| CA | 950833 A1 | 7/1974 |

(Continued)

OTHER PUBLICATIONS

Ouellet et al, J.Vet.Intern.Med., 23:258-263 (Year: 2009).*
Liu et al., "Pharmacology Preparation Technology." Chemical Industry Press, 2006, pp. 113-114.
Sun et al., "Pimobendan." Chemical Industry Press, 2002, pp. 29-30.
Matsumori et al., "Pharmacology letters: Accelerated Communication: Pimobendan inhibits the activation of transcription factor NF-kB A mechanism which explains its inhibition of cytokine production and inducible nitric oxide synthase". Life Sciences, vol. 67, 2000, pp. 2513-2519.
McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp. 54-59. Originally published online Jun. 23, 2003, http://circ.ahajournals.org, 7 pages.
Medline, homogeneous, Merriam-Webster, Last Accessed Feb. 10, 2011, 1 page, http://www.merriam-webster.com/medlineplus/homogeneous.

(Continued)

*Primary Examiner* — Sudhakar Katakam
(74) *Attorney, Agent, or Firm* — Judy Jarecki-Black

(57) ABSTRACT

The invention relates to pimobendan for use in a method of reducing the heart size and/or delaying the onset of clinical symptoms in a patient suffering from asymptomatic (occult, preclinical) heart failure, preferably congestive heart failure, due to mitral valve disease (MVD), and/or delaying the onset of heart failure, preferably congestive heart failure, in a patient suffering from asymptomatic (occult, preclinical) heart failure, preferably congestive heart failure, due to mitral valve disease (MVD), wherein the patient is preferably a mammal, more preferably a human, a dog, a cat or a horse, and most preferably a dog.

24 Claims, No Drawings

(56) References Cited

U.S. PATENT DOCUMENTS

| | | |
|---|---|---|
| 2003/0162835 A1 | 8/2003 | Staniforth et al. |
| 2003/0165565 A1 | 9/2003 | Mehta |
| 2003/0190343 A1 | 10/2003 | Thombre et al. |
| 2003/0212114 A1 | 11/2003 | Sato |
| 2004/0037869 A1 | 2/2004 | Cleverly et al. |
| 2004/0152664 A1 | 8/2004 | Chang et al. |
| 2004/0157887 A1 | 8/2004 | Whittle et al. |
| 2005/0095293 A1 | 5/2005 | Brauns et al. |
| 2005/0203097 A1 | 9/2005 | Folger et al. |
| 2005/0239692 A1 | 10/2005 | Lindenblatt et al. |
| 2007/0112010 A1 | 5/2007 | Kleeman et al. |
| 2008/0207629 A1 | 8/2008 | Folger et al. |
| 2009/0082282 A1 | 3/2009 | Daemmgen et al. |
| 2010/0035889 A1* | 2/2010 | Daemmgen ........ A61K 31/4166 514/252.06 |
| 2010/0166857 A1 | 7/2010 | Yan et al. |
| 2010/0183718 A1 | 7/2010 | Ovaert et al. |
| 2010/0273807 A1 | 10/2010 | Kleeman et al. |
| 2011/0028457 A1 | 2/2011 | Roewer et al. |
| 2011/0189283 A1 | 8/2011 | Derrieu et al. |
| 2011/0251208 A1 | 10/2011 | Daemmgen et al. |
| 2011/0318420 A1 | 12/2011 | Hu et al. |
| 2012/0148640 A1 | 6/2012 | Folger et al. |
| 2012/0308662 A1 | 12/2012 | Konishi et al. |
| 2013/0115301 A1 | 5/2013 | Bele et al. |
| 2013/0203690 A1 | 8/2013 | Daemmgen et al. |
| 2014/0155338 A1 | 6/2014 | Daemmgen et al. |
| 2014/0235648 A1 | 8/2014 | Folger et al. |
| 2014/0363510 A1 | 12/2014 | Folger et al. |
| 2015/0025082 A1 | 1/2015 | Aven et al. |
| 2015/0064249 A1 | 3/2015 | Folger et al. |
| 2015/0148335 A1 | 5/2015 | Bova et al. |
| 2015/0150820 A1 | 6/2015 | Laczay |
| 2016/0038420 A1 | 2/2016 | Brunel et al. |
| 2017/0290829 A1 | 10/2017 | Schummer et al. |

FOREIGN PATENT DOCUMENTS

| | | |
|---|---|---|
| CA | 1222697 A1 | 6/1987 |
| CA | 2034569 A1 | 7/1991 |
| CA | 1336498 C | 8/1995 |
| CN | 1662250 A | 8/2005 |
| CN | 1702243 A | 11/2005 |
| DE | 3728244 A1 | 3/1989 |
| DE | 4001623 A1 | 7/1991 |
| EP | 0241179 A1 | 10/1987 |
| EP | 0256566 A1 | 2/1988 |
| EP | 0268146 A1 | 5/1988 |
| EP | 0306846 A2 | 3/1989 |
| EP | 0330052 A2 | 8/1989 |
| EP | 0335545 A2 | 10/1989 |
| EP | 0349657 A1 | 1/1990 |
| EP | 439030 A2 | 7/1991 |
| EP | 1123703 A1 | 8/2001 |
| EP | 1247456 A2 | 10/2002 |
| EP | 1260215 A1 | 11/2002 |
| EP | 1579862 A1 | 9/2005 |
| EP | 1903039 A1 | 3/2008 |
| EP | 1920785 A1 | 5/2008 |
| EP | 2338493 A1 | 6/2011 |
| EP | 3034071 A1 | 6/2016 |
| FR | 2350105 A1 | 12/1977 |
| GB | 1045031 A | 10/1966 |
| GB | 2228004 A | 8/1990 |
| JP | 61500788 A | 4/1986 |
| JP | H029825 A | 1/1990 |
| JP | H0489428 A | 3/1992 |
| JP | H0570612 A | 3/1993 |
| JP | H11228302 A | 8/1999 |
| JP | 2005281283 A | 10/2005 |
| JP | 2007191419 A | 8/2007 |
| JP | 2008504308 A | 2/2008 |
| JP | 2011157390 A | 8/2011 |
| JP | 2012533595 A | 12/2012 |
| JP | 2013006798 A | 1/2013 |
| JP | 2013503113 A | 1/2013 |
| WO | 1985002767 A1 | 7/1985 |
| WO | 1989004178 A1 | 5/1989 |
| WO | 1995031963 A1 | 11/1995 |
| WO | 0012137 A1 | 3/2000 |
| WO | 2000069414 A2 | 11/2000 |
| WO | 2001035925 A1 | 5/2001 |
| WO | 2001064190 A1 | 9/2001 |
| WO | 2001097861 A2 | 12/2001 |
| WO | 0245693 A1 | 6/2002 |
| WO | 2002049646 A1 | 6/2002 |
| WO | 2003012030 A2 | 2/2003 |
| WO | 03072141 A1 | 9/2003 |
| WO | 2003074032 A1 | 9/2003 |
| WO | 2003075895 A1 | 9/2003 |
| WO | 2003097067 A1 | 11/2003 |
| WO | 2003099194 A2 | 12/2003 |
| WO | 2004000317 A1 | 12/2003 |
| WO | 2004000344 A1 | 12/2003 |
| WO | 2004016252 A1 | 2/2004 |
| WO | 2004033444 A1 | 4/2004 |
| WO | 2004050657 A2 | 6/2004 |
| WO | 2004058726 A2 | 7/2004 |
| WO | 2004060353 A1 | 7/2004 |
| WO | 2004089418 A1 | 10/2004 |
| WO | 2005035505 A2 | 4/2005 |
| WO | 2005084647 A1 | 9/2005 |
| WO | 2005092343 A1 | 10/2005 |
| WO | 2005107756 A1 | 11/2005 |
| WO | 2005117911 A2 | 12/2005 |
| WO | 2006000229 A2 | 1/2006 |
| WO | 2006022562 A1 | 3/2006 |
| WO | 2006060122 A2 | 6/2006 |
| WO | 2006060127 A2 | 6/2006 |
| WO | 2007036671 A2 | 4/2007 |
| WO | 2007038796 A1 | 4/2007 |
| WO | 2007054514 A2 | 5/2007 |
| WO | 2007112274 A2 | 10/2007 |
| WO | 2007128749 A1 | 11/2007 |
| WO | 2008055871 A1 | 5/2008 |
| WO | 2009060226 A1 | 5/2009 |
| WO | 2010010257 A2 | 1/2010 |
| WO | 2010055119 A2 | 5/2010 |
| WO | 2010060874 A1 | 6/2010 |
| WO | 2011009818 A1 | 1/2011 |
| WO | 2011042463 A2 | 4/2011 |
| WO | 2011076738 A1 | 6/2011 |
| WO | 2013024023 A1 | 2/2013 |
| WO | 2013135852 A1 | 9/2013 |
| WO | 2013164473 A1 | 11/2013 |
| WO | 2013170317 A1 | 11/2013 |
| WO | 2014136035 A1 | 9/2014 |
| WO | 2015082389 A1 | 6/2015 |
| WO | 2017174571 A1 | 10/2017 |

OTHER PUBLICATIONS

Menard et al., "Physico-Chemical Aspects of the Complexation of Some Drugs with Cyclodextrins". Drug Development and Industrial Pharmacy, vol. 16, No. 1, 1990, pp. 91-113.

Merriam-Webster, homogeneous, Last Accessed Feb. 10, 2011, 2 pages, http://www.merriam-webster.com/dictionary/homogeneous.

Monnet et al., "Idiopathic Dilated Cardiomyopathy in Dogs: Survival and Prognostic Indicators". 1995, Journal of Veterinary Internal Medicine, vol. 9, No. 1, pp. 12-17.

Nakamoto et al., "The role of ascorbic acid deficiency in human gingivitis—a new hypothesis". Journal of Theoretical Biology, vol. 108, No. 2, May 1984, pp. 163-171.

Ng, Tien M.H., "Levosimendan, a New Calcium-Sensitizing Inotrope for Heart Failure". Pharmacotherapy, vol. 24, No. 10, 2004, pp. 1366-1384.

O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.

Ohte et al., "The Cardia Effects of Pimobendan (But Not Amrinone) Are Preserved at Rest and During Exercise in Conscious Dogs with

(56) References Cited

OTHER PUBLICATIONS

Pacing-Induced Heart Failure". The Journal of Pharmacology and Experimental Therapeutics, vol. 282, No. 1, 1997, pp. 23-31.

Okazaki et al., "A genetic linkage map of the Syrian hamster and localization of cariomyopathy locus on chromosome 9qa2.1-b1 using RLGS spot-mapping". Nature Genetics, vol. 13, May 1996, pp. 87-90.

Packer et al., "Effect of Oral Milrinone on Mortality in Severe Chronic Heart Failure." The New England Journal of Medicine, vol. 325, No. 21, Nov. 1991, pp. 1468-1475.

Pagel et al., "Comparison of the effects of levosimendn, pimobendan, and milrinone on canine left ventricular-arterial coupling and mechanical efficiency". Basic Respiratory Cardiology, vol. 91, 1996, pp. 296-307.

Pagel et al., "Influence of levosimendan, pimobendan, and milrinone on the regional distribution of cardiac output in anaesthetized dogs". British Journal of Pharmacology, vol. 119, 1996, pp. 609-615.

Permanetter et al., "Acute Effects of Intraveneous UD-CG 115 BS (Pimobendan) on the Cardiovascular System and Left Ventricular Pump Function". Journal of Cardiovascular Pharmacology, vol. 14, Supp. 2, 1989, pp. S36-S40.

Pernsteiner et al., "Effect of Topical Application of Phenylephrine Hydrochloride on Hyperplastic Gingivitis". Journal of Periodontology, vol. 48, No. 8, Aug. 1977, pp. 473-477.

Petit et al., "Vetmedin® 1.25 mg, Vetmedin® 5 mg, Chewable tablets, Inodilator (pimobendan) tablet for dogs". Dictionary of Veterinary Drugs and Animal Health Products Marketed in France, 16th Edition, Les Editions du Point Vétérinaire, 2011, pp. 1658-1661.

Phillips et al., "The challenge of gene therapy and DNA delivery". Journal of Pharmacy and Pharmacology, vol. 53, 2001, pp. 1169-1174.

Piel et al., "Development of a parenteral and of an oral formulation of albendazole with cyclodextrins". S.T.P. Pharma Sciences, vol. 9, No. 3, 1999, pp. 257-260.

Pirollo et al., "Targeted Delivery of Small Interfering RNA: Approaching Effective Cancer Therapies". Cancer Research, vol. 68, No. 5, Mar. 2008, pp. 1247-1250.

Rackley, Charles E., "Diseases of the Heart and Pericardium"., The Merck Manual, Chapter 25, 16th Edition, 1992, pp. 446-459.

Redenti et al., "Drug/Cyclodextrin/Hydroxy Acid Multicomponent Systems. Properties and Pharmaceutical Applications". Journal of Pharmaceutical Sciences, vol. 89, 2000, pp. 1-8.

Remme et al., "Hemodynamic Effects of Intravenous Pimobendan in Patients with Left Ventricular Dysfunction". Journal of Cardiovascular Pharmacology, vol. 15, Supp. 2, 1989, pp. S41-S44.

Remme et al., "Hemodynamic, Neurohumoral, and Myocardial Energetic Effects of Pimobendan, a Novel Calcium-Sensitizing Compound, in Patients with Mild to Moderate Heart Failure". Journal of Cardiovascular Pharmacology, vol. 24, No. 5, 1994, pp. 730-739.

Rinsyo to Kenkyu, "A case of diastolic hypertrophic cardiomyopathy in which sinus bradycardia and associated cardiac failure were improved as a result of cilostazol administration." The Japanese Journal of Clinical and Experimental Medicine, vol. 83, No. 5, May 2006, pp. 125-130.

Rodriguez, Damon B., "Treatment of Feline Hypertrophic Cardiomyopathy*". Compendium, vol. 24, No. 6, Jun. 2002, pp. 470-476.

Roland et al., "The Use of Pimobendan in Feline Heart Failure Secondary to Spontaneous Heart Disease". The 18th Annual ECVIM Congress, Abstract, Belgium, Sep. 2008, 1 page.

Rudnic et al., "Oral Solid Dosage Forms". Remington: The Science and Practice of Pharmacy, 20th Edition, Lippincott Williams & Wilkins, Baltimore, Maryland, Chapter 45, 2000, pp. 858-870.

Saavedra et al., "Reverse Remodeling and Enhanced Adrenergic Reserve From Passive External Support in Experimental Dilated Heart Failure". Journal of the American College of Cariology, vol. 39, No. 12, 2002, pp. 2069-1076.

Sabbah et al., "Effects of long-term monotherapy with enalapril, metoprolol, and digoxin on the progression of left ventricular dysfuntion and dilation in dogs with reduced ejection fraction". Circulation, vol. 89, 1994, pp. 2852-2859.

Sabbah, Hani N., "The Cardiac Support Device and the Myosplint: Treating Heart Failure by Targeting Left Ventricular Size and Shape". The Annals of Thoracic Surgery, vol. 75, 2003, pp. S13-S19.

Shiga et al., "b-Blocker Therapy Combined with Low-Dose Pimobendan in Patients with Idiopathic Dilated Cardiomyopathy and Chronic Obstructive Pulmonary Disease: Report on Two Cases". Cardiovascular Drugs and Therapy, vol. 16, 2002, pp. 259-263.

Sisson et al., "Myocardial Diseases of Dogs". Textbook of Canine and Feline Cardiology: Principles and Clinical Practice, Second Edition, Chapter 27, Saunders, 1999, pp. 581-619.

Sisson, David, "Lecture Notes: Cardiology", The District of Columbia Academy of Veterinary Medicine, May 2001, pp. 1-18.

Stuber et al., "The Pharmaceutical and Biological Availability of Commercial Preparations of Furosemide". Arzneimittel-Forschung, vol. 32, No. 6, 1982, pp. 693-697.

Summerfield et al., "Efficacy of Pimobendan in the Prevention of Congestive Heart Failure or Sudden Death in Doberman Pinschers with Preclinical Dilated Cardiomyopathy (The PROTECT Study)". Journal of Veterinary Internal Medicine, vol. 26, 2012, pp. 1337-1349.

Takeda et al., "Normalization of Left Ventricular Parameters Following Combined Pimobendan and Carvedilol Treatment in a Case of Unclassified Cardiomyopathy with Longstanding Refractory Status". Internal Medicine, vol. 41, No. 12, Dec. 2002, pp. 1147-1152.

The American Heritage Dictionary, homogeneous, Last Accessed Feb. 10, 2011, 1 page, http://www.xreferplus.com/entry/hmdictenglang/homogeneous.

Thiel et al., "Content uniformity of microdose tablets (dosage 1 μg-10 mg) produced by fluid bed granulation of interactive mixtures". Journal of Pharmacy and Pharmacology, vol. 38, 1986, pp. 335-343.

Tomanek et al., "Growth of the Coronary Vasculature in Hypertrophy: Mechanisms and Model Dependence". Cellular and Molecular Biology Research, vol. 40, No. 2, 1994, pp. 129-136.

Trendelenburg, U. "The Action of Histamine and 5-Hydroxytryptamine on Isolated Mammalian Atria". The Journal of Pharmacology and Experimental Therapeutics, vol. 130, No. 4, Dec. 1960, pp. 450-460.

Van Meel et al., "Pimobendan Increases Survival of Cardiomyopathic Hamsters". Journal of Cardiovascular Pharmacology, vol. 13, 1989, pp. 508-509.

Vidal et al., "Making sense of antisense". European Journal of Cancer, vol. 41, 2005, pp. 2812-2818.

Villar et al., "Ibuprofen, Aspirin and Acetaminophen Toxicosis and Treatment in Dogs and Cats". Veterinary and Human Toxicology, vol. 40, No. 3, Jun. 1998, pp. 156-162.

Wikipedia, the Free Encyclopedia, "Milrinone". [Accessed at: http://en.wikipedia.org/wiki/Milrinone on Mar. 10, 2014].

Wikipedia, the Free Encyclopedia, "Pimobendan". [Accessed at: http://en.wikipedia.org/wiki/Pimobenan on Mar. 10, 2014].

Woolley et al., "Effects of Treatment Type on Vertebral Heart Size in Dogs With Myxomatous Mitral Valve Disease". The Journal of Applied Research in Veterinary Medicine, vol. 5, No. 1, 2007, pp. 43-48.

Fox et al., "Bradykinin-evoked sensitization of airway sensory nerves: A mechanism for ACE-inhibitor cough." Nature Medicine, vol. 2, No. 7, Jul. 1996, pp. 814-817.

International Search Report and Written Opinion for PCT/EP2017/057970 dated Jun. 12, 2017.

Vromans et al., "Densification properties and compactibility of mixtures of pharmaceutical excipients with and without magnesium stearate." International Journal of Pharmaceutics, vol. 46, 1988, pp. 183-192.

"905 Uniformity of Dosage Units". 2011 The United States Pharmacopeial Convention, Stage 6 Harmonization, Dec. 1, 2011, pp. 1-3.

(56) References Cited

OTHER PUBLICATIONS

"Cardiovascular system". MIMS, IVS Annual, Chapter 5, 2003, p. 104.
"Citric Acid". The Merck Index, An Encyclopedia of Chemicals, Drugs, and Biologicals, 13th Edition, Merck Research Laboratories Division of Merck & Co., Inc., Whitehouse Station, NJ, Index 2350, 2001, pp. 405-406.
"Guidance for Industry, Container Closure Systems for Packaging Human Drugs and Biologics: Chemistry, Manufacturing, and Controils Documentation". U.S. Department of Health and Human Services Food and Drug Administration, May 1999, pp. 1-56.
"Pharmaceutical Necessities". Remington's Pharmaceutical Sciences, 18th Edition, Mack Publishing Company, Easton, Pennsylvania, Chapter 66, 1990, pp. 1288-1300.
"Pimobendan". The Merck Index, An Encyclopedia of Chemicals, Drugs, and Biologicals, 13th Edition, Merck Research Laboratories Division of Merck & Co., Inc., Whitehouse Station, NJ, Index 7515, 2001, p. 1332.
"Rimadyl F 50 mg". Summary of Product Characteristics, Zoetis France, May 15, 2013, pp. 1-4.
"Vetmedin®—1,25 mg appetizing tablets for dogs Veterinary use". Summary of Product Characteristics, SCS Boehringer Ingelheim Comm. V, Mar. 25, 2009, pp. 1-4.
Abstract in English for CN1702243A, 2005.
Abstract in English for DE3728244,1989.
Abstract in English for EP0306846, 1989.
Abstract in English for EP0330052, 1989.
Abstract in English for JP2005281283, 2005.
Abstract in English for JPH0489428, 1992.
Abstract in English of JPH0570612, 1993.
Abstract in English of JPH11228302, 1999.
Ahmed et al., "Pharmaceutical challenges in veterinary product development". Advanced Drug Delivery Reviews, vol. 54, 2002, pp. 871-882.
Asanoi et al., "Disparate Inotropic and Lusitropic Responses to Pimobendan in Conscious Dogs with Tachycardia-Induced Heart Failure". Journal of Cardiovascular Pharmacology, vol. 23, No. 2, 1994, pp. 268-274.
Ash et al., "Receptor Mediating Some Actions of Histamine". British Journal of Pharmacology and Chemotherapy, vol. 27, No. 2, Aug. 1996, pp. 427-439.
Atkins et al., "Guidelines for the Diagnosis and Treatment of Canine Chronic Valvular Heart Disease". Journal of Veterinary Internal Medicine, vol. 23, No. 6, 2009, pp. 1-9.
Banker et al., "Uniformity of Dosage Units". Modern Pharmaceutics, Fourth Edition, Revised and Expanded, Marcel Dekker, Inc., New York, NY, 2006, p. 498.
Bassani et al., "Enhanced Water-Solubility of Albendazole by Hydroxy-Propyl-ß-Cyclodextrin Complexation". Journal of Inclusion Phenomena and Molecular Recognition in Chemistry, vol. 25, No. 1-3, Mar. 1996, pp. 149-152.
Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.
Baur et al., "Cardiac remodelling and myocardial contractility in patients with congestive heart failure treated with furosemide and enalapril". Basic Research in Cardiology, vol. 86, Supp. 1, 1991, pp. 157-163.
Beers, et al., Merck Manual of Diagnosis and Therapy, 17th Edition, Chapter 203, Section 16, Merck Research Laboratories, Whitehouse Station, NJ, USA, 1999, pp. 1688-1692.
Berny et al., "Review: Animal Poisoning in Europe. Part 2: Companion Animals". The Veterinary Journal, vol. 193, 2010, pp. 255-259.
Black et al., "Definition and Antagonism of Histamine H2-receptors". Nature, vol. 236, Apr. 1972, pp. 385-390.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Borgarelli et al., "Canine Idiopathic Dilated Cardiomyopathy. Part II: Pathophysiology and therapy". The Veterinary Journal, vol. 162, 2001, pp. 182-195.
Bozzone, Scott, "Solid Oral Dosage Forms Powder Blending" and "Solid Oral Dosage Forms, Blend Uniformity: Principles and Examples". Pfizer, IKEV Meeting, May 31, 2001, pp. 1-66.
Brewster et al., "Cyclodextrins as pharmaceutical solubilizers". Advanced Drug Delivery Reviews, vol. 59, No. 7, 2007, pp. 645-666.
Buchanan et al. "Vertebral scale system to measure canine heart size in radiographs". Journal of the American Veterinary Medical Association, vol. 206, No. 2, Jan. 1995, pp. 194-199.
Burlage et al., "Other Pharmaceutical Adjuncts"., Physical and Technical Pharmacy, The Blakiston Division: The McGraw-Hill Book Company, Inc., New York, 1963, pp. 653-662.
Calvert et al., "Congestive cardiomyopathy in Doberman Pinscher dogs". Journal of the American Veterinary Medical Association, vol. 181, 1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Cambridge Dictionary, homogeneous, Last Accessed Feb. 10, 2011, 1 page, http://dictionary.cambridge.org/dictionary/british/homogeneous.
Chambers 21st Century Dictionary, homogeneous, Last Accessed Feb. 10, 2011, 1 page, http://www.xreferplus.com/entry/chambdict/homogeneous.
Chetboul, et al., "Comparitive Adverse Cardiac Effects of Pimobendan and Benazepril Monotherapy in Dogs with Mild Degenerative Mitral Valve Disease: A Prospective, Controlled, Blinded, and Randomized Study". Journal of Veterinary Internal Medicine, vol. 21, 2007, pp. 742-753.
Choy et al., "Scaling of myocardial mass to flow and morphometry of coronary arteries". Journal of Applied Physiology, vol. 104, 2008, pp. 1281-1286.
Cohn et al., "Cardiac Remodeling—Concepts and Clinical Implications: A Consensus Paper From an International Forum on Cardiac Remodeling". Journal of the American College of Cardiology, vol. 35, No. 3, 2000, pp. 569-582.
Collins English Dictionary, homogeneous, Last Accessed Feb. 10, 2011, 1 page, http://xreferplus.com/entry/hcengdict/homogeneous.
Conlon, P.D., "Nonsteroidal Drugs Used in the Treatment of Inflammation". Veterinary Clinics of North America: Small Animal Practice, vol. 18, No. 6, Nov. 1988, pp. 1115-1131.
Cowley et al, "Treatment of severe heart failure: quantity or quality of life? A trial of enoximone"., British Heart Journal, vol. 72, 1994, pp. 226-230.
Côté et al., "Congestive Heart Failure". Feline Cardiology, Ch. 19, Wiley-Blackwell, ISBN 978-0-8138-1242-7, 2011, p. 259.
Deneke et al., "Medikamentöse Therapie der Herzinsuffizienz". Herzschr Elektrophys, vol. 15, Suppl. 1, 2004, pp. 1/74-1/80.
Dews et al., "The Antihistamine Substance 2786 R.P." British Journal of Pharmacology, vol. 1, 1946, pp. 278-286.
Dictionary of Veterinary Drugs and Animal Health Products Marketed in France, 12th Edition, 2003, 3 pages.
El-Hagrasy et al., "A Process Analytical Technology Approach to Near-Infrared Process Control of Pharmaceutical Power Blending: Part II: Qualitative Near-Infrared Models for Prediction of Blend Homogeneity". Journal of Pharmaceutical Sciences, vol. 95, No. 2, Feb. 2006, pp. 407-421.
El-Hagrasy et al., "Near-Infrared Spectroscopy and Imaging for the Monitoring of Powder Blend Homogeneity". Journal of Pharmaceutical Sciences, vol. 90, No. 9, Sep. 2001,. pp. 1298-1307.
Elliott, P., "Diagnosis and management of dilated cardiomyopathy". Heart, vol. 83, 2000, pp. 106-112.
Endoh, Masao, "New Aspects of the Treatment of Myocardial Failure from a Pharmacological Standpoint". Journal of Clinical and Experimental Medicine, vol. 187, No. 10, 1998, pp. 827-831.

(56) References Cited

OTHER PUBLICATIONS

Erhardt, L., "An Emerging Role for Calcium Sensitisation in the Treatment of Heart Failure". Expert Opinion on Investigational Drugs, vol. 14, No. 6, 2005, pp. 659-670.

Ettinger et al., "Effects of enalapril maleate on survival of dogs with naturally acquired heart failure". Journal of the American Veterinary Medical Association, vol. 213, No. 11, 1998, pp. 1573-1577.

Ettinger et al., "Therapeutic Considerations in Medicine and Disease". Textbook of Veterinary Internal Medicine, Diseases of the Dog and Cat, Sixth Edition, vol. I, 2004, pp. 530-531.

Fitton et al., "Pimobendan. A Review of its Pharmacology and Therapeutic Potential in Congestive Heart Failure". Drugs and Aging, vol. 4, No. 5, 1994, pp. 417-441.

Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.

Fox, Philip R., "Hypertrophic Cardiomyopathy. Clinical and Pathologic Correlates". Journal of Veterinary Cardiology, vol. 5, No. 2, Nov. 2003, pp. 39-45.

Fraker et al., "Reversal of phosphate induced decreases in force by the benzimidazole pyridazinone, UD-CG 212 CL, in myofilaments from human ventricle." Molecular and Cellular Biochemistry, vol. 176, 1997, pp. 83-88.

Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.

Fujino et al., "Differential Effects of d- and I-Pimobendan on Cardia Myofilament Calcium Sensitivity". The Journal of Pharmacology and Experimental Therapeutics, vol. 247, No. 2, 1988, pp. 519-523.

Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.

Groban, Leanne, "Diastolic Dysfunction in the Older Heart". Journal of Cardiothoracic and Vascular Anesthesia, vol. 19, No. 2, Apr. 2005, pp. 228-236.

Gwathmey et al., "Abnormal Intracellular Calcium Handling in Myocardium From Patients With End-Stage Heart Failure". Circulation Research, vol. 61, No. 1, 1987, pp. 70-76.

Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, 1989, pp. 225-233.

Hauf et al., "Acute and Long-Term Hemodynamic Effects of Pimobendan (UD-CG 115 BS) in Comparison with Captopril". Journal of Cardiovascular Pharmacology, vol. 15, Supp. 2, 1989, pp. S49-S56.

Hemati et al., "Fluidized bed coating and granulation: influence of process-related variables and physicochemical properties on the growth kinetics". Powder Technology, vol. 13, 2002, pp. 18-34.

Häggstrom et al., "Effect of Pimobendan or Benazepril Hydrochloride on Survival Times in Dogs with Congestive Heart Failure Caused by Naturally Occurring Myxomatous Mitral Valve Disease: The QUEST Study". Journal of Veterinary Internal Medicine, vol. 22, 2008, pp. 1124-1135.

Häggstrom et al., "Longitudinal Analysis of Quality of Life, Clinical, Radiographic, Echocardiographic, and Laboratory Variables in Dogs with Myxomatous Mitral Valve Disease Rexceiving Pimobendan or Benazepril: The QUEST Study". Journal of Veterinary Internal Medicine, 2013, pp. 1-11.

Häggström et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.

Häggström et al., "New insights into degenerative mitral valve disease in dogs". Veterinary Clinics Small Animal Practice, vol. 34, 2004, pp. 1209-1226.

Iwasaki et al., "Pimobendan Inhibits the Production of Proinflammatory Cytokines and Gene Expression of Inducible Nitric Oxide Synthase in a Murine Model of Viral Myocarditis". Journal of the American College of Cardiology, vol. 33, No. 5, 1999, pp. 1400-1407.

Jain et al., "Effects of Milrinone on Left Ventricular Remodeling After Acute Myocardial Infarction". Circulation, vol. 84, No. 2, Aug. 1991, pp. 798-804.

Kashem et al., "CardioClasp: A New Passive Device to Reshape Cardiac Enlargement". ASAIO Journal, vol. 48, No. 3, 2002, pp. 253-259.

Kato et al., "Clinical Evaluation of Pimobendan (UD-CG115BS) for Chronic Heart Failure—A Multicentre Placebo-Controlled Double Blind Study". Journal of Clinical Therapeutics & Medicines, vol. 8, No. 6, 1992, pp. 1311-1351.

Kato, Kazuzo, "Clinical Efficacy and Safety of Pimobendan in Treatment of Heart Failure-Experience in Japan". Cardiology, vol. 88, Supp. 2, 1997, pp. 28-36.

Katz et al., "A multicenter, randomized, double-blind, placebo-controlled trial of pimobendan, a new cardiotonic and vasodilator agent, in patients with severe congestive heart failure". American Heart Journal, vol. 123, 1992, pp. 95-103.

Kittleson et al., "The Acute Hemodynamic Effects of Milrinone in Dogs With Severe Idiopathic Myocardial Failure". Journal of Veterinary Medicine, vol. 1, 1987, pp. 121-127.

Kitzen et al., "Pimobendan". Cardiovascular Drug Reviews, vol. 6, No. 4, 1988, pp. 265-291.

Koob et al., "Acute Effects of Furosemide on Blood Electrolytes and Hemodynamics in Dogs". Angiology, 1978, pp. 463-472.

Kubo et al, "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.

Kvart et al., "Efficacy of Enalapril for Prevention of Congestive Heart Failure in Dogs with Myxomatous Valve Disease and Asymptomatic Mitral Regurgitation". Journal of Veterinary Internal Medicine, vol. 16, 2002, pp. 80-88.

Lachman et al., "The Theory and Practice of Industrial Pharmacy"., 3rd Edition, Lea & Febiger, Philadelphia, 1986, pp. 58-60.

Lai et al., "Real Time and Noninvasive Monitoring of Dry Powder Blend Homogeneity". AIChE Journal, vol. 47, No. 11, Nov. 2001, pp. 2618-2622.

Lamb et al., "Assessment of the value of the vertebral heart scale in the radiographic diagnosis of cardia disease in dogs". Veterinary Record, vol. 146, 2000, pp. 687-690.

Lantz et al., "Stability of nizatidine in extemporaneous oral liquid preparations". American Journal of Hospital Pharmacy, vol. 47, No. 12, Dec. 1990, pp. 2716-2719.

Lewis et al., "Near-Infrared Chemical Imaging for Product and Process Understanding". In Process Analytical Technology, Second Edition, John Wiley & Sons, Ltd., United Kingdom, 2010, pp. 272-276.

Lewis, Alan B., "Clinical Profile and Outcome of Restrictive Cardiomyopathy in Children". American Heart Journal, vol. 123, No. 6, 1992, pp. 1589-1593.

Lezcano et al., "Complexation of Several Benzimidazole-Type Fungicides with Alpha and Beta-Cyclodextrins". Journal of Agricultural and Food Chemistry, vol. 50, 2002, pp. 108-112.

Lip et al., "ABC of heart failure: Aetiology". British Medical Journal, vol. 320, Jan. 2000, pp. 104-107.

Liu et al., "Cardiovascular Pathology: The Role of Cardiovascular Pathology in Practice". Textbook of Canine and Feline Cardiology: Principles and Clinical Practice, Second Edition, Chapter 36, Saunders, 1999, pp. 817-844.

Loew, Earl R., "Gastric Secretion in Dogs Treated with Histamine Antagonist, Thymoxyethyldiethylamine". Experimental Biology and Medicine, vol. 48, No. 1, Oct. 1941, pp. 65-68.

Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.

Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, Jul./Aug. 2006, pp. 249-261.

(56) References Cited

OTHER PUBLICATIONS

Lombard, Christophe W., "Therapy of Congestive Heart Failure in Dogs with Pimobendan". Proceedings of the 18th Annual Veterinary Medical Forum, American College of Veterinary International Medicine, Seattle, WA, 2000, pp. 107-109.

Lord et al., "Radiology: Role of Radiology in Diagnosis and Management of Thoracic Disease". Textbook of Canine and Feline Cardiology: Principles and Clinical Practice, Second Edition, Chapter 7, Saunders, 1999, pp. 111-117.

Luis-Fuentes, Virginia, "The effect of pimobendan in English Cocker Spaniels and Doberman dogs with heart failure and idiopathic dilated cardiomyopathy (DCM)". Ingelheimer Dialog, Boehringer Inglehim Vetmedica GmbH, Jun. 2000, Frankfort/Mainz, pp. 8-11.

Lyon et al., "Near-Infrared Spectral Imaging for Quality Assurance of Pharmaceutical Products: Analysis of Tablets to Assess Powder Blend Homogeneity". AAPS PharmSciTech, vol. 3, No. 3, Art. 17, Sep. 2002, pp. 1-15.

Malik et al., "Permethrin Spot-On Intoxication of Cats: Literature review and survey of veterinary practitioners in Australia". Journal of Feline Medicine and Surgery, vol. 12, 2010, pp. 5-14.

Mamoru et al., "Effects of Long-term, Very-low-dose Pimobendan for Patients with Diastolic Heart Failure". Journal of Cardial Failure, vol. 12, No. 8, Oct. 2006, p. S171.

Bourezg et al., "Redispersible lipid nanoparticles of Spironolactone obtained by three drying methods." Colloids and Surfaces A: Physicochemical and Engineering Aspects, vol. 413, 2012, pp. 191-199.

El-Badry et al., "Physicochemical Characterization and Dissolution Properties of Meloxicam-Gelucire 50/13 Binary Systems." Scientia Pharmaceutica, vol. 79, 2011, pp. 375-386.

Fasinu et al., "Diverse approaches for the enhancement of oral drug bioavailability." Biopharmaceutics & Drug Disposition, vol. 32, 2011, pp. 185-209.

Lindenberg et al., "Classification of orally administered drugs on the World Health Organization Model list of Essential Medicines according to the biopharmaceutics classification system." European Journal of Pharmaceutics and Biopharmaceutics, vol. 58, 2004, pp. 265-278.

Nainar et al., "Biopharmaceutical Classification System in In-vitro/In-vivo Correlation: Concept and Development Strategies in Drug Delivery." Tropical Journal of Pharmaceutical Research, vol. 11, No. 2, Apr. 2012, pp. 319-329.

Upadhyay et al., "Formulation of Fast-Release Gastroretentive Solid Dispersion of Glibenclamide with Gelucire 50/13." Tropical Journal of Pharmaceutical Research, vol. 11, No. 3, Jun. 2012, pp. 361-369.

Vasconcelos et al., "Solid dispersions as strategy to improve oral bioavailability of poor water soluble drugs." Drug Discovery Today, vol. 12, Nos. 23/24, Dec. 2007, pp. 1068-1075.

Ouellet et al., "Effect of Pimobendan on Echocardiographic Values in Dogs with Asymptomatic Mitral Valve Disease." Journal of Veterinary Internal Medicine, vol. 23, 2009, pp. 258-263.

Kanno et al., "Effects of Pimobendan for Mitral Valve Regurgitation in Dogs." Journal of Veterinary Medical Science, vol. 69, No. 4, Apr. 2007, pp. 373-377.

Atkins et al., "Pharmacologic management of myxomatous mitral valve disease in dogs." Journal of Veterinary Cardiology, vol. 14, 2012, pp. 165-184.

Boswood et al., "Evaluation of pimobendan in dogs with cardiomegaly caused by preclinical mitral valve disease." The Veterinary Record, vol. 168, No. 8, Feb. 2011, p. 222.

Boswood et al., "Effect of Pimobendan in Dogs with Preclinical Myxomatous Mitral Valve Disease and cardiomegaly the EPIC Study—A Randomized Clinical Trial." Journal of Veterinary Internal Medicine, vol. 30, 2016, pp. 1765-1779.

Beaufrere et al., "Therapeutic Review: Pimobendan." Journal of Exotic Pet Medicine, vol. 18, No. 4, Oct. 2009, pp. 311-313.

\* cited by examiner

USE OF PIMOBENDAN FOR THE REDUCTION OF HEART SIZE AND/OR THE DELAY OF ONSET OF CLINICAL SYMPTOMS IN PATIENTS WITH ASYMPTOMATIC HEART FAILURE DUE TO MITRAL VALVE DISEASE

FIELD OF THE INVENTION

The invention relates to the field of medicine, particularly veterinary medicine. In particular, the invention relates to the use of pimobendan for the reduction of heart size in patients with asymptomatic (occult, preclinical) heart failure (HF) due to (myxomatous) mitral valve disease [(M)MVD] and/or chronic valvular heart disease (CVHD; also known as chronic valve disease, CVD) and/or atrial ventricular valvular insufficiency (AVVI) and/or for the delay of onset of clinical symptoms in patients with asymptomatic (occult, preclinical) HF due to (m)MVD and/or CVHD/CVD and/or AVVI, and/or the delay of onset of heart failure due to (myxomatous) mitral valve disease [(M)MVD] and/or chronic valvular heart disease (CVHD; also known as chronic valve disease, CVD) and/or atrial ventricular valvular insufficiency (AVVI).

BACKGROUND OF THE INVENTION

Heart failure is divided in different stages, which were defined by different classification systems, e.g. the International Small Animal Cardiac Health Council (ISACHC), the New York Heart Association (NYHA) functional classification systems and the currently used classification according to the Consensus Statements of the American College of Veterinary Internal Medicine (ACVIM), 2009.

Classification according to the International Small Animal Cardiac Health Council (ISACHC) System:

Class I: asymptomatic (also known as occult or preclinical)

Class IA: no evidence of compensation for underlying heart disease (no volume overload or pressure overload detected radiographically or echocardiographically)

Class IB: clinical signs of compensation for underlying heart disease (volume overload or pressure overload detected radiographically or echocardiographically)

Class II: mild to moderate heart failure with clinical signs at rest or with mild exercise (treatment required)

Class III: advanced heart failure; clinical signs of severe congestive heart failure Class IIIA: home treatment possible Class IIIB: requires hospitalization New York Heart Association (NYHA) functional classification system:

Class I: describes patients with asymptomatic heart disease (e.g., chronic valvular heart disease (CVHD) is present, but no clinical signs are evident even with exercise).

Class II: describes patients with heart disease that causes clinical signs only during strenuous exercise.

Class III: describes patients with heart disease that causes clinical signs with routine daily activities or mild exercise.

Class IV: describes patients with heart disease that causes severe clinical signs even at rest.

The ACVIM system describes four basic stages of heart disease and failure:

Stage A: patients at high risk for developing heart disease but that currently have no identifiable structural disorder of the heart (e.g., every Cavalier King Charles Spaniel without a heart murmur).

Stage B: patients with structural heart disease (e.g., the typical murmur of mitral valve regurgitation is present), but that have never developed clinical signs caused by heart failure (because of important clinical implications for prognosis and treatment, the panel further subdivided Stage B into Stage B1 and B2).

Stage B1: asymptomatic patients that have no radiographic or echocardiographic evidence of cardiac remodeling in response to CVHD.

Stage B2: asymptomatic patients that have hemodynamically significant valve regurgitation, as evidenced by radiographic or echocardiographic findings of left-sided heart enlargement.

Stage C: patients with past or current clinical signs of heart failure associated with structural heart disease.

Stage D: patients with end-stage disease with clinical signs of heart failure caused by CVHD that are refractory to "standard therapy".

The pathology of the heart begins with ISACHC Class I, NYHA Class I and ACVIM stage B2 in which cardiac murmur or cardiac chamber enlargement, but no clinical symptoms are present (ISACHC Class I or asymptomatic/occult/preclinical stage). Clinical symptoms become manifest in the course of progression of the disease (ISACHC Class II or III, NYHA class II, III or IV, ACVIM stage C and D).

Known progression of (M)MVD or CVHD/CVD or AVVI heart failure is associated with an increase of the heart size. Cardiac remodeling due to the morphologic changes within the heart is generally considered as a risk factor and is linked to worsening of pathophysiologic changes of the heart leading to heart failure. One goal of the therapy of heart failure is the reduction of the heart size and the delay of morphological changes of the heart.

A known pharmaceutically active compound to treat heart failure is pimobendan (4,5-dihydro-6-[2-(4-methoxyphenyl)-1H-benzimidazol-5-yl]-5-methyl-3(2H)-pyridazinone) disclosed in EP 0 008 391 and having the formula:

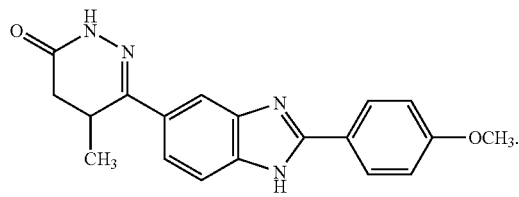 [SMILES: COc1ccc(-c2nc3cc(C4=NNC(=O)CC4C)ccc3[nH]2)cc1]

Pimobendan is a well-known compound for the treatment of congestive heart failure (CHF) originating for example from dilated cardiomyopathy (DCM) or mitral valve disease (MVD) in animals, especially dogs. Pimobendan is also approved as a drug product for cardiovascular treatment in humans in Japan.

Several publications disclose the use of pimobendan in the treatment of heart failure in animals, such as, for instance, the following ones.

WO 2005/092343 describes the use of PDE-III inhibitors, such as pimobendan, for the reduction of heart size of a patient suffering from heart failure without, however, mentioning patients with asymptomatic (occult, preclinical) heart failure due to mitral valve disease (MVD).

Lombard and co-workers (Lombard C W et al., J Am Anim Hosp Assoc 2006, 42: 249-261) disclose the clinical efficacy of pimobendan versus benazepril for the treatment of the clinical acquired atrioventricular valvular disease in dogs.

WO 2007/054514 is directed to the use of PDE-III inhibitors, such as pimobendan, for the treatment of asymptomatic (also known as occult or preclinical) heart failure without, however, mentioning patients with asymptomatic (occult, preclinical) heart failure due to mitral valve disease (MVD).

Häggström J et al. (J Vet Intern Med 2008, 22: 1124-1135) describe the effect of pimobendan or benazepril hydrochloride on survival times in dogs with clinical congestive heart failure caused by naturally occurring myxomatous mitral valve disease without, however, mentioning patients with asymptomatic (occult, preclinical) heart failure due to mitral valve disease (MVD).

Summerfield N J and co-workers (Summerfield N J et al., J Vet Intern Med 2012, 26: 1337-1349) relate to a clinical study on the efficacy of pimobendan in the prevention of congestive heart failure or sudden death in Doberman Pinschers with preclinical dilated cardiomyopathy (DCM). However, they are silent about patients with asymptomatic (occult, preclinical) heart failure due to mitral valve disease (MVD).

Häggström J et al. (J Vet Intern Med 2013, 27: 1452-1462) describe short-term hemodynamic and neuroendocrine effects of pimobendan and benazepril in dogs with clinical myxomatous mitral valve disease and congestive heart failure. However, they are silent about patients with asymptomatic (occult, preclinical) heart failure due to mitral valve disease (MVD).

Internet website www.epictrial.com is directed to the EPIC trial, a study to investigate the effects of pimobendan in the delay of onset of clinical symptoms of congestive heart failure due to mitral valve disease (MVD). However, at the priority dates of this patent application this trial was still ongoing and no study results were publically available.

Several other publications, however, relate to the disadvantageous cardiac effects of pimobendan treatment, such as the following ones.

Schneider P et al. (Exp Toxic Pathol 1997, 49: 217-224) describe the comparative cardiac toxicity of the IV administered pimobendan in female Beagle dogs.

Tissier R and co-workers (Tissier R et al., Cardiovascular Toxicology 2005, 5(1): 43-51) disclose adverse effects increased mitral valve regurgitation and myocardial hypertrophy in two dogs with long-term (chronic) clinical pimobendan therapy.

Amsallem E et al. (Cochrane Database Syst Rev 2005, 25: 1) found that phosphodiesterase inhibitors, such as among others pimobendan, are associated with a significant 17% increased mortality rate in human patients and in addition significantly increase cardiac death, sudden death, arrhythmias and vertigos. The authors conclude that chronic use of phosphodiesterase inhibitors should be avoided in heart failure patients.

Chetboul V and co-workers (Chetboul V et al., J Vet Intern Med 2007, 21: 742-753) show the results of a prospective, controlled, blinded and randomized study on the comparative adverse cardiac effects of pimobendan and benazepril monotherapy in dogs with mild degenerative asymptomatic mitral valve disease.

Ouellet M et al. (J Vet Intern Med 2009, 23: 258-263) describe the effect of pimobendan on echocardiographic values in dogs with asymptomatic mitral valve disease. However, this study failed to identify beneficial long-term changes in the severity of mitral regurgitation after addition of pimobendan to ACE inhibitor treatment.

The objective underlying the present invention is, therefore, to provide a medical treatment which overcomes the problems of the prior art as described above.

SUMMARY OF THE INVENTION

The present invention concerns pimobendan for use in a method of reducing the heart size and/or delaying the onset of clinical symptoms in a patient suffering from asymptomatic (occult, preclinical) heart failure due to mitral valve disease (MVD), preferably asymptomatic (occult, preclinical) congestive heart failure due to mitral valve disease (MVD), more preferably asymptomatic (occult, preclinical) congestive heart failure due to myxomatous mitral valve disease (MMVD), and/or delaying the onset of heart failure in a patient suffering from asymptomatic (occult, preclinical) heart failure due to mitral valve disease (MVD), preferably delaying the onset of congestive heart failure in a patient suffering from asymptomatic (occult, preclinical) heart failure due to mitral valve disease (MVD), more preferably delaying the onset of congestive heart failure in a patient suffering from asymptomatic (occult, preclinical) heart failure due to myxomatous mitral valve disease (MMVD).

Corresponding methods of reducing the heart size and/or delaying the onset of clinical symptoms in a patient suffering from asymptomatic (occult, preclinical) heart failure due to mitral valve disease (MVD) and/or delaying the onset of (congestive) heart failure in a patient suffering from asymptomatic (occult, preclinical) heart failure due to mitral valve disease (MVD) and uses for the preparation of a pharmaceutical composition/medicament for reducing the heart size and/or delaying the onset of clinical symptoms in a patient suffering from asymptomatic (occult, preclinical) heart failure due to mitral valve disease (MVD) and/or delaying the onset of heart failure, preferably congestive heart failure, in a patient suffering from asymptomatic (occult, preclinical) heart failure due to mitral valve disease (MVD) are also intended to be within the scope of the present invention.

The present invention further concerns pimobendan for use in a method of reducing the heart size and delaying the onset of clinical symptoms in a patient suffering from asymptomatic (occult, preclinical) heart failure due to mitral valve disease (MVD), preferably asymptomatic (occult, preclinical) congestive heart failure due to mitral valve disease (MVD), more preferably asymptomatic (occult, preclinical) congestive heart failure due to myxomatous mitral valve disease (MMVD), and delaying the onset of heart failure in a patient suffering from asymptomatic (occult, preclinical) heart failure due to mitral valve disease (MVD), preferably delaying the onset of congestive heart failure in a patient suffering from asymptomatic (occult, preclinical) heart failure due to mitral valve disease (MVD), more preferably delaying the onset of congestive heart failure in a patient suffering from asymptomatic (occult, preclinical) heart failure due to myxomatous mitral valve disease (MMVD).

Corresponding methods of reducing the heart size and delaying the onset of clinical symptoms in a patient suffering from asymptomatic (occult, preclinical) heart failure due to mitral valve disease (MVD) and/or delaying the onset of (congestive) heart failure in a patient suffering from asymptomatic (occult, preclinical) heart failure due to mitral valve disease (MVD) and uses for the preparation of a pharmaceutical composition/medicament for reducing the heart size and delaying the onset of clinical symptoms in a patient suffering from asymptomatic (occult, preclinical) heart failure due to mitral valve disease (MVD) and delaying the onset of heart failure, preferably congestive heart failure, in a patient suffering from asymptomatic (occult, preclinical) heart failure due to mitral valve disease (MVD) are also intended to be within the scope of the present invention.

The advantages of the medical use(s) of pimobendan according to the present invention are as follows:

Prolongation of the preclinical (also known as asymptomatic or occult) phase without exhibiting clinical symptoms of congestive heart failure Delay of onset of (clinical symptoms of) congestive heart failure Increase of survival time of the treated patients as compared to placebo treatment Improvement of the quality of life of the treated patients Reduction of heart size of the treated patients as compared to baseline (i.e. before start of treatment)

Improving cardiac function/output in the treated patients

Reduction of sudden cardiac death/euthanasia of patients due to cardiac reasons

Risk reduction of reaching congestive heart failure

Any previously raised concerns regarding the safety of the medication should be allayed by the longer survival observed in the pimobendan group in the all-cause mortality analysis. There was no difference between groups in the rate or type of potential adverse events observed. This is despite the fact that dogs in the pimobendan group spent longer time in the study and were therefore at risk of experiencing adverse events for a longer period.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The term "patient" as used hereinabove and herein below relates to an animal or a person suffering from (congestive) heart failure. The term "patient" embraces mammals such as primates including humans. In addition to primates, a variety of other mammals can be treated according to the method of the present invention. For instance, mammals, including but not limited to, horses, dogs, cats, or equine, canine, feline species can be treated. Preferred are human patients, dogs, cats and horses. Human patients are female or male person who are suffering from heart failure. As a rule such persons are children, young adults, adults or elderly people with an age of between 6 and 80, preferably between 30 and 65 years. Most preferred are dogs.

The term heart failure", preferably "congestive heart failure", as used hereinabove and herein below relates to any contractile disorder or disease of the heart. Clinical manifestations are as a rule the results of changes to the heart's cellular and molecular components and to mediators that drive homeostatic control. The heart failure, preferably congestive heart failure, is as a rule accompanied by an increase of the heart size and deterioration of cardiac functions.

The term "reduction of the heart size" as used hereinabove and herein below relates to a reduction of the size of the heart of the patient, which is diagnosed using echocardiography and which may be determined according to the radiograph methods suggested by James W. Buchanan et al. (Buchanan J W et al., J Am Vet Med Assoc 1995, 206(2), 194-199) and is expressed in the relative change of the vertebral heart size. Preferably, the relative heart size of said patient is reduced by at least 5%, preferably at least 10%, 15%, 20%, 25% or at least 30%, compared to baseline, i.e. before pimobendan treatment is initiated, more preferably within 10 to 100 days, even more preferably within about 30 to 40 days, most preferably within about 35 days of treatment with pimobendan.

The term "asymptomatic (occult, preclinical) (congestive) heart failure due to mitral valve disease (MVD)" as used hereinabove and herein below relates to any contractile disorder or disease of the heart which is due to/secondary to MVD—however, yet without any clinical symptoms of (congestive) heart failure. In particular, it relates to heart failure of ISACHC Class I (Class IA and/or Class IB), NYHA Class I and ACVIM stage B2.

The terms "delay of onset of clinical symptoms" and "prolongation of time until onset of clinical symptoms" are interchangeably used hereinabove and herein below and relate to the time period between from diagnosing the morphological changes of the heart of the patient until the beginning of clinical symptoms of heart failure, preferably congestive heart failure, due to mitral valve disease (MVD). In particular, they relate to the prolongation of time from still asymptomatic (occult, preclinical) heart failure of ISACHC Class I (Class IA and/or Class IB), NYHA Class I and ACVIM stage B2 to clinical evident heart failure, preferably congestive heart failure, of ISACHC Class II and further to Class III (Class IIIA and/or Class IIIB), NYHA Class II, III and IV and ACVIM stage C and D.

For the sake of unambiguity in the course of the present invention the medicinal indication terms "mitral valve disease (MVD)", "myxomatous mitral valve disease (MMVD)", "chronic valvular heart disease (CVHD)", "chronic valve disease (CVD)" and "atrial ventricular valvular insufficiency (AVVI)" are all interchangeably used. As for ISACHC Class I (Class IA and/or Class IB), NYHA Class I and ACVIM stage B2 heart failure they are all synonymous to each other and have the identical medicinal meaning.

The term "risk reduction of reaching congestive heart failure" as used hereinabove and herein below relates to the relative risk of experiencing the clinical evident heart failure, preferably congestive heart failure. Preferably, the relative risk is reduced by at least 5%, preferably at least 10%, 15%, 20%, 25% or at least 30%.

The term "effective amount" as used herein means an amount sufficient to achieve a reduction of the heart size in patients with asymptomatic (occult, preclinical) heart failure (HF) due to mitral valve disease (MVD) and/or to achieve the delay of onset of clinical symptoms in patients with asymptomatic (occult, preclinical) HF due to MVD and/or to achieve the delay of onset of heart failure, preferably congestive heart failure, in patients with asymptomatic (occult, preclinical) HF due to MVD, when pimobendan is administered in a single dosage form.

In one aspect, the present invention relates to pimobendan for use according to the hereinabove and herein below disclosed aspects and preferred embodiments, wherein the asymptomatic (occult, preclinical) heart failure due to mitral valve disease (MVD), preferably asymptomatic (occult, preclinical) congestive heart failure due to mitral valve disease MVD, more preferably asymptomatic (occult, preclinical) congestive heart failure due to myxomatous mitral valve disease (MMVD) is of stage ISACHC Class I, preferably ISACHC Class IA or Class IB, more preferably of stage ISACHC Class IB, NYHA Class I and ACVIM stage B2.

In another aspect, the present invention relates to pimobendan for use according to the hereinabove and herein below disclosed aspects and preferred embodiments, wherein the pimobendan treatment effects a reduction of the heart size of the already pathologically enlarged heart of the patient. In other words, such patient suffers from asymptomatic (occult, preclinical) heart failure due to mitral valve disease (MVD) of ISACHC Class I (Class IA and/or Class IB), NYHA Class I and ACVIM stage B2 and already has a pathologically enlarged heart (e.g. visible by means of echocardiography), but does not yet show any clinical symptoms of heart failure, preferably congestive heart failure.

In another aspect, the present invention relates to pimobendan for use according to the hereinabove and herein below disclosed aspects and preferred embodiments, wherein the pimobendan treatment effects a prolongation of the time of survival of the patient as compared to placebo treatment or non-pimobendan treatment. In this connection, non-pimobendan treatment refers to a comparison treatment where the respective patient group receives an active pharmaceutical ingredient other than pimobendan instead of pimobendan or a placebo. Preferably such pimobendan treatment effects a prolongation of the time of survival of the patient of at least 30 days, more preferably at least 2 months, even more preferably at least 3 months, even more preferably at least 4 months, even more preferably at least 5 months, even more preferably at least 6 months, even more preferably at least 7 months, even more preferably at least 8 months, even more preferably at least 9 months, even more preferably at least 10 months, even more preferably at least 11 months, even more preferably at least 12 months, even more preferably at least 13 months, even more preferably at least 14 months, even more preferably at least 15 months, as compared to placebo treatment or non-pimobendan treatment.

In another aspect, the present invention relates to pimobendan for use according to the hereinabove and herein below disclosed aspects and preferred embodiments, wherein the pimobendan treatment effects a prolongation of the preclinical phase without exhibiting clinical symptoms of congestive heart failure, effects a delay of onset of (clinical symptoms of) congestive heart failure, increases the survival time of the treated patients as compared to placebo treatment, improves the quality of life of the treated patients, leads to a reduction of heart size of the treated patients as compared to baseline (i.e. before start of treatment), improves cardiac function/output in the treated patients, reduces sudden cardiac death/euthanasia of patients due to cardiac reasons and/or reduces the risk of reaching congestive heart failure.

In another aspect, the present invention relates to pimobendan for use according to the hereinabove and herein below disclosed aspects and preferred embodiments, wherein the patient is a mammal, preferably a human, a dog, a cat or a horse, more preferably a dog.

The dosage regimen for pimobendan will, of course, vary depending upon known factors, such as the pharmacodynamic characteristics and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, delay or arrest the progress of the disorder.

By way of general guidance, the daily oral dosage of pimobendan, when used for the indicated effects, will range between about 0.2 mg/kg to 0.6 mg/kg bodyweight SID, in particular from 0.2 mg/kg to 0.6 mg/kg bodyweight of pimobendan administered per day (EU) and 0.5 mg/kg bodyweight of pimobendan administered per day (US).

Preferably, the daily pimobendan dose is administered as two doses of 0.1 mg/kg to 0.3 mg/kg bodyweight, preferably two doses of 0.1 mg/kg to 0.3 mg/kg bodyweight every 12 hours (EU), more preferably two doses of 0.25 mg/kg bodyweight every 12 hours (USA).

In yet another aspect, the present invention relates to pimobendan for use according to the hereinabove and herein below disclosed aspects and preferred embodiments, wherein pimobendan is administered in a daily dose of 0.2 mg/kg to 0.6 mg/kg bodyweight SID, in particular from 0.2 mg/kg to 0.6 mg/kg bodyweight of pimobendan administered per day (EU) and 0.5 mg/kg bodyweight of pimobendan administered per day (US).

Preferably, the daily pimobendan dose is administered as two doses of 0.1 mg/kg to 0.3 mg/kg bodyweight, preferably two doses of 0.1 mg/kg to 0.3 mg/kg bodyweight every 12 hours (EU), more preferably two doses of 0.25 mg/kg bodyweight every 12 hours (USA).

According to another aspect of the present invention, pimobendan is administered in combination with at least one second active pharmaceutical ingredient (API). Such at least one second API is preferably selected from the group consisting of, afterload reducers (arteriodilators) such as ACE inhibitors, preload reducers (venodilators) such as diuretics, platelet inhibitors, beta blockers and angiotensin II antagonists, aldosterone antagonists, antiarrhythmic agents (if arrhythmias occur) and/or diuretics, in particular, wherein the ACE inhibitor is selected from the group consisting of omapatrilat, MDL100240, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and/or spirapril; and/or wherein the afterload reducer (arteriodilator) is selected from the group consisting of hydralazine, calcium channel blockers diltiazem, verapamil, and amlodipine, nitroprusside, and phosphodiesterase inhibitors such as sildenafil; and/or wherein the beta blocker is selected from the group consisting of bisoprolol, carvedilol, metoprolol, propranolol, atenolol, esmolol, and/or timolol; and/or wherein the platelet inhibitor is selected from the group consisting of aspirin, clopidogrel, factor Xa inhibitors, heparin, and low molecular weight heparins; and/or wherein the angiotensin II antagonist is selected from the group consisting of saralasin acetate, candesartan, cilexetil, valsartan, candesartan, losartan potassium, eprosartan, irbesartan, tasosartan, pomisartan and/or telmisartan; and/or wherein the aldosterone antagonist is selected from the group consisting of spironolactone, triampterene, eplerenone, canrenone, potassium canrenone; and/or wherein the antiarrhythmic agents are selected from the group consisting of amiodarone, betrylium, disopyramide, dofetilide, flecainide, ibutilide, mexiletine, tocainide, procainamide, lidocaine, propafenone, diltiazem, verapamil, digoxin, *digitalis*, quinidine and/or sotalol; and/or wherein the diuretic is selected from the group consisting of furosemide, spironolactone, torasemide, bumetanide, etacrynic acid, azosemide, muzolimine, piretanide, tripamide, bendroflumethazide, chlorothiazide, hydrochlorothiazide, hydroflumethiazide, methychlothiazide, polythiazide, trichlormethiazide, chlorthialidone, indapamide, metolazone, quinethazone, etozolin, triamterene and/or amiloride; and/or wherein the preload reducer (venodilator) agents are selected from the group consisting of nitroglycerine, nitroprusside, and isorbide; and/or wherein the positive inotropic agents are selected from the group consisting of dobutamine, digoxin, *digitalis*, dopamine, amrinone, and milrinone; and/or wherein the hyperpolarization-activated cyclic nucleotide-gated (HCN) channel blockers or negative chronotropic agents are selected from the group consisting of cilobradine, ivabradine, and adenosine Preferably, pimobendan is administered together with one or more API selected from the group consisting of one or more ACE inhibitors and one or more diuretics.

In yet another aspect, the present invention relates to pimobendan for use according to the hereinabove and herein below disclosed aspects and preferred embodiments, wherein pimobendan is administered before, during or after administration of one or more additional active pharmaceutical ingredients selected from the group consisting of ACE inhibitors, preferably benazepril; and diuretics, preferably furosemide. More preferably, pimobendan is administered concomitantly with benazepril and furosemide.

Pimobendan can be administered in such oral dosage forms as tablets, chewable tablets, chews, capsules (each of which includes sustained release or timed release formulations), pills, powders, granules, elixirs, tinctures, suspensions, solutions, syrups, and emulsions. It may also be administered in intravenous (bolus or infusion), intraperitoneal, subcutaneous, or intramuscular form, all using dosage forms well known to those of ordinary skill in the pharmaceutical arts. It can be administered alone, but generally will be administered with a pharmaceutical carrier selected on the basis of the chosen route of administration and standard pharmaceutical practice.

In another aspect, the present invention relates to pimobendan for use according to the hereinabove and herein below disclosed aspects and preferred embodiments, wherein pimobendan is administered orally or parenterally, preferably orally, more preferably orally in the form of a tablet or capsule, most preferably orally in the form of a tablet.

Pimobendan can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

Pimobendan is typically administered in admixture with suitable pharmaceutical diluents, excipients and/or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatine, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Pimobendan can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pimobendan can also be administered in lipid-coated form as part of a solid pharmaceutical formulation (see for instance WO 2015/082389).

Pimobendan may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues.

Furthermore, Pimobendan may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and cross linked or amphipathic block copolymers of hydrogels.

Dosage forms (pharmaceutical compositions) suitable for administration may contain from about 1 milligram to about 100 milligrams of active ingredient per dosage unit.

In these pharmaceutical compositions the active ingredient will ordinarily be present in an amount of about 0.5-95% by weight based on the total weight of the composition.

Gelatine capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Where two or more of the foregoing second APIs are administered with pimobendan, generally the amount of each component in a typical daily dosage and typical dosage form may be reduced relative to the usual dosage of the API when administered alone, in view of the additive or synergistic effect of the APIs when administered in combination.

Particularly when provided as a single dosage unit, the potential exists for a chemical interaction between the combined APIs. For this reason, when pimobendan and at least one second API are combined in a single dosage unit they are formulated such that although the APIs are combined in a single dosage unit, the physical contact between the APIs is minimized (that is, reduced). For example, one API may be enteric coated. By enteric coating one of the APIs, it is possible not only to minimize the contact between the combined APIs, but also, it is possible to control the release of one of these components in the gastrointestinal tract such that one of these components is not released in the stomach but rather is released in the intestines. One of the APIs may also be coated with a material which effects a sustained-release throughout the gastrointestinal tract and also serves to minimize physical contact between the combined APIs.

Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

EXAMPLES

The following examples serve to further illustrate the present invention; but the same should not be construed as a limitation of the scope of the invention disclosed herein.

Example 1—Interim Analysis Data

Previous studies have suggested that pimobendan treatment significantly reduces case fatality and morbidity in dogs with CHF. The potential benefit of pimobendan treatment in delaying the progression of asymptomatic (occult, preclinical) heart failure in dogs due to mitral valve disease (MVD) has not yet been demonstrated.

Pimobendan is a benzimidazopyridazinone with a potent positive inotropic and a vasodilatory effect. This combined effect of preload and afterload reduction, together with positive inotropic support, results in a reduction in cardiac size and filling pressures in the heart of dogs with occult heart failure due to mitral valve disease.

The administration of pimobendan to dogs suffering from asymptomatic (occult, preclinical) heart failure due to mitral valve disease (MVD) prolongs the time to the onset of clinical signs of congestive heart failure by approx. 359 days (12.0 months) compared to placebo and extends survival time (all-cause mortality) by approx. 168 days (5.6 months) compared to placebo. Treatment of dogs in the preclinical phase of heart failure with pimobendan therefore leads to improved outcome.

Example 2—Preliminary Analysis of Final Study Results

Preliminary analysis of the final results of a blinded, placebo controlled study of 360 dogs shows that administration of pimobendan to dogs with MMVD and echocardiographic and radiographic evidence of cardiomegaly results in the prolongation of the preclinical period and is safe and well tolerated.

Median time to the primary endpoint is 1228 days (95% CI 856—NA) in the pimobendan group and 766 days (95% CI 667-875) in the placebo group (P=0.0038). Prolongation of the preclinical period by approximately 15 months represents a substantial clinical benefit.

Overall survival, as determined by All Cause Mortality is also significantly longer in the pimobendan group than in the placebo group (P=0.012), and this also represents a significant clinical benefit.

Pimobendan also causes a reduction in heart size, compared to the placebo group, when measured over the first 35 days of the study (P<0.0001).

The final study results have been published in the meantime (Boswood A et al., J Vet Intern Med 2016, 30(6): 1765-1779).

REFERENCES (1) Amsallem E et al., Cochrane Database Syst Rev 2005, 25: 1
(2) Boswood A et al., J Vet Intern Med 2016, 30(6): 1765-1779
(3) Buchanan J W et al., J Am Vet Med Assoc 1995, 206(2), 194-199
(4) Chetboul V et al., J Vet Intern Med 2007, 21: 742-753
(5) EP 0 008 391
(6) Häggström J et al., J Vet Intern Med 2008, 22: 1124-1135
(7) Häggström J et al., J Vet Intern Med 2013, 27: 1452-1462
(8) Lombard C W et al., J Am Anim Hosp Assoc 2006, 42: 249-261
(9) Ouellet M et al., J Vet Intern Med 2009, 23: 258-263
(10) Schneider P et al., Exp Toxic Pathol 1997, 49: 217-224
(11) Summerfield N J et al., J Vet Intern Med 2012, 26: 1337-1349
(12) Tissier R et al., Cardiovascular Toxicology 2005, 5(1): 43-51
(13) WO 2005/092343
(14) WO 2007/054514

(15) WO 2015/082389
(16) www.epictrial.com

The invention claimed is:

1. A method for treating a patient suffering from asymptomatic (occult, preclinical) heart failure due to mitral valve disease (MVD) or myxomatous mitral valve disease (MMVD), the method comprising administering to the patient an effective amount of a pharmaceutical composition comprising pimobendan so as to effect a reduction of the heart size of an already pathologically enlarged heart of the patient in combination with delaying the onset of clinical symptoms of heart failure in the patient.

2. The method of claim 1, wherein one or both of the asymptomatic (occult, preclinical) heart failure due to mitral valve disease (MVD) and asymptomatic (occult, preclinical) heart failure due to myxomatous mitral valve disease (MMVD) is of a stage selected from the group consisting of: stage ISACHC Class I, ISACHC Class IA or Class IB, stage ISACHC Class IB, NYHA Class I and ACVIM stage B2.

3. The method of claim 1, wherein the administration of pimobendan results in a reduction of the heart size of the already pathologically enlarged heart of the patient of at least 5%, as compared to a baseline prior to pimobendan treatment.

4. The method of claim 1, wherein the administration of pimobendan results in one or more of the following in the patient selected from the group consisting of: effects a prolongation of the preclinical phase without exhibiting clinical symptoms of heart failure, effects a delay of onset of (clinical symptoms of) heart failure, increases the survival time of the treated patient as compared to placebo treatment, improves the quality of life of the treated patient, a reduction of heart size of the treated patient as compared to baseline (before start of treatment), improves cardiac function/output in the treated patient, reduces sudden cardiac death/euthanasia of the patient due to cardiac reasons, and reduces the risk of reaching heart failure.

5. The method claim 1, wherein the patient is a mammal selected from the group consisting of: a human, a dog, a cat, and a horse.

6. The method of claim 1, wherein pimobendan is administered in a daily dose of 0.2 mg/kg to 0.6 mg/kg bodyweight.

7. The method of claim 6, wherein the daily pimobendan dose is administered as two doses of 0.1 mg/kg to 0.3 mg/kg bodyweight, wherein two doses of 0.1 mg/kg to 0.3 mg/kg bodyweight are administered every 12 hours, or two doses of 0.25 mg/kg bodyweight are administered every 12 hours.

8. The method of claim 1, wherein pimobendan is administered orally or parenterally.

9. A method for treating a patient suffering from asymptomatic (occult, preclinical) heart failure due to mitral valve disease (MVD) or myxomatous mitral valve disease (MMVD), the method comprising administering to the patient an effective amount of a pharmaceutical composition comprising pimobendan concomitantly with one or more additional active pharmaceutical ingredients selected from the group consisting of ACE inhibitors and diuretics so as to effect a reduction of the heart size of an already pathologically enlarged heart of the patient in combination with delaying the onset of clinical symptoms of heart failure in the patient.

10. The method of claim 9, wherein pimobendan is administered concomitantly with benazepril and/or furosemide.

11. The method of claim 1, wherein pimobendan is administered orally in the form of a tablet or a capsule.

12. The method of claim 9, wherein the one or more additional active pharmaceutical ingredients comprises benazepril.

13. The method of claim 9, wherein the one or more additional active pharmaceutical ingredients comprises furosemide.

14. The method of claim 1, wherein the administration of pimobendan results in a reduction of the heart size of the already pathologically enlarged heart of the patient of at least 20%, as compared to a baseline prior to pimobendan treatment.

15. The method of claim 1, wherein the administration of pimobendan results in a reduction of the heart size of the already pathologically enlarged heart of the patient of at least 30%, as compared to a baseline prior to pimobendan treatment.

16. The method of claim 1, wherein the administration of pimobendan effects a prolongation of the time of survival of the patient as compared to placebo treatment or non-pimobendan treatment, of at least about 5 months.

17. The method of claim 1, wherein the administration of pimobendan effects a prolongation of the time of survival of the patient as compared to placebo treatment or non-pimobendan treatment, of at least about 7 months.

18. The method of claim 1, wherein the delaying the onset of clinical symptoms of heart failure in the patient or the reduction in heart size of the patient in combination with delaying the onset of clinical symptoms of heart failure in the patient is for a period of at least about 12 months.

19. The method of claim 9, wherein the delaying the onset of clinical symptoms of heart failure in the patient or the reduction in heart size of the patient in combination with delaying the onset of clinical symptoms of heart failure in the patient is for a period of at least about 12 months.

20. The method of claim 1, wherein one or both of the asymptomatic (occult, preclinical) heart failure due to mitral valve disease (MVD) and asymptomatic (occult, preclinical) heart failure due to myxomatous mitral valve disease (MMVD) is of ISACHC Class D3 or ACVIM stage B2.

21. The method of claim 9, wherein one or both of the asymptomatic (occult, preclinical) heart failure due to mitral valve disease (MVD) and asymptomatic (occult, preclinical) heart failure due to myxomatous mitral valve disease (MMVD) is of ISACHC Class D3 or ACVIM stage B2.

22. The method of claim 1, wherein the administration of pimobendan further effects a prolongation of the time of survival of the patient, as compared to placebo treatment or non-pimobendan treatment, of at least about 30 days.

23. The method of claim 22, wherein the administration of pimobendan effects a prolongation of the time of survival of the patient, as compared to placebo treatment or non-pimobendan treatment, of at least about 5 months.

24. The method of claim 22, wherein the administration of pimobendan effects a prolongation of the time of survival of the patient, as compared to placebo treatment or non-pimobendan treatment, of at least about 7 months.

* * * * *

UNITED STATES PATENT AND TRADEMARK OFFICE
CERTIFICATE OF CORRECTION

PATENT NO. : 10,537,570 B2
APPLICATION NO. : 15/477188
DATED : January 21, 2020
INVENTOR(S) : Christoph Schummer and Olaf Joens It is certified that error appears in the above-identified patent and that said Letters Patent is hereby corrected as shown below:

In the Claims

Claim 20, Column 14, Line 44, "(MMVD) is of ISACHC Class D3 or ACVIM stage B2" should read --(MMVD) is of ISACHC Class IB or ACVIM stage B2--;

Claim 21, Column 14, Line 49, "(MMVD) is of ISACHC Class D3 or ACVIM stage B2" should read --(MMVD) is of ISACHC Class IB or ACVIM stage B2--.

Signed and Sealed this
Ninth Day of June, 2020

Andrei Iancu
*Director of the United States Patent and Trademark Office*